(12) United States Patent
Itai (10) Patent No.: US 9,390,497 B2
(45) Date of Patent: Jul. 12, 2016

(54) MEDICAL IMAGE PROCESSING APPARATUS, METHOD AND PROGRAM

(71) Applicant: FUJIFILM Corporation, Tokyo (JP)

(72) Inventor: Yoshinori Itai, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/477,738

(22) Filed: Sep. 4, 2014

(65) Prior Publication Data

US 2014/0369578 A1    Dec. 18, 2014

Related U.S. Application Data

(63) Continuation of application No. PCT/JP2013/001309, filed on Mar. 4, 2013.

(30) Foreign Application Priority Data

Mar. 9, 2012    (JP) .................. 2012-052413

(51) Int. Cl.
| | |
|---|---|
| G06K 9/00 | (2006.01) |
| G06T 7/00 | (2006.01) |
| A61B 6/03 | (2006.01) |
| A61B 6/00 | (2006.01) |
| G06T 19/00 | (2011.01) |

(Continued)

(52) U.S. Cl.
CPC ................ *G06T 7/0012* (2013.01); *A61B 1/00* (2013.01); *A61B 6/032* (2013.01); *A61B 6/466* (2013.01); *A61B 6/50* (2013.01); *A61B 6/5211* (2013.01); *G06K 9/2054* (2013.01); *G06T 19/003* (2013.01); *G06T 19/20* (2013.01); *G06T 2200/04* (2013.01); *G06T 2207/10068* (2013.01); *G06T 2207/20148* (2013.01); *G06T 2207/30028* (2013.01); *G06T 2207/30061* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 7,369,691 | B2 | 5/2008 | Kondo et al. |
| 7,889,900 | B2 | 2/2011 | Weese et al. |

(Continued)

FOREIGN PATENT DOCUMENTS

| | | | |
|---|---|---|---|
| JP | 2000-135215 A | 5/2000 |
| JP | 2004-180940 A | 7/2004 |

(Continued)

OTHER PUBLICATIONS

International Search Report (ISR) (PCT Form PCT/ISA/210), in PCT/JP2013/001309, dated Jul. 16, 2013.

(Continued)

*Primary Examiner* — Stephen R Koziol
*Assistant Examiner* — Amandeep Saini
(74) *Attorney, Agent, or Firm* — McGinn IP Law Group PLLC (57) ABSTRACT

A three-dimensional image is obtained, and a relative degree of interest is set at each of plural positions on a path connecting the plural positions in the three-dimensional image. A discrimination condition for identifying, based on the set degree or degrees of interest, a virtual endoscopic image or images to be generated from the three-dimensional image is obtained, and only the virtual endoscopic image or images identified based on the discrimination condition are generated based on the three-dimensional image.

16 Claims, 4 Drawing Sheets

(51) Int. Cl.
  *G06K 9/20* (2006.01)
  *G06T 19/20* (2011.01)
  *A61B 1/00* (2006.01)

(56) References Cited

U.S. PATENT DOCUMENTS

| | | | | |
|---|---|---|---|---|
| 2005/0151730 | A1* | 7/2005 | Lobregt | G06T 15/10 |
| | | | | 345/419 |
| 2008/0183073 | A1* | 7/2008 | Higgins | G06T 19/003 |
| | | | | 600/425 |
| 2009/0054729 | A1 | 2/2009 | Mori et al. | |
| 2009/0226057 | A1* | 9/2009 | Mashiach | G06T 5/008 |
| | | | | 382/128 |
| 2011/0242097 | A1* | 10/2011 | Miyamoto | G06T 15/08 |
| | | | | 345/419 |
| 2012/0053408 | A1* | 3/2012 | Miyamoto | 600/109 |
| 2012/0230559 | A1* | 9/2012 | Itai | G06T 7/0026 |
| | | | | 382/128 |
| 2013/0113802 | A1* | 5/2013 | Weersink et al. | 345/427 |
| 2013/0250081 | A1* | 9/2013 | Pandey | H04N 7/18 |
| | | | | 348/77 |

FOREIGN PATENT DOCUMENTS

| | | |
|---|---|---|
| JP | 2004-283373 A | 10/2004 |
| JP | 2006-20874 A | 1/2006 |
| JP | 2008-529578 A | 8/2008 |
| WO | WO 99/42977 A1 | 8/1999 |
| WO | WO 2005/069223 A2 | 7/2005 |
| WO | WO 2007/129616 A1 | 11/2007 |

OTHER PUBLICATIONS

Extended European Search Report dated Oct. 12, 2015.

* cited by examiner

MEDICAL IMAGE PROCESSING APPARATUS, METHOD AND PROGRAM

CROSS-REFERENCE TO RELATED APPLICATIONS

This application is a Continuation of PCT International Application No. PCT/JP2013/001309 filed on Mar. 4, 2013, which claims priority under 35 U.S.C. §119(a) to Japanese Patent Application No. 2012-052413 filed on Mar. 9, 2012. Each of the above applications is hereby expressly incorporated by reference, in its entirety, into the present application.

BACKGROUND OF THE INVENTION

1. Field of the Invention

The present invention relates to techniques for assisting on image-based diagnosis using plural virtual endoscopic images generated from a three-dimensional image.

2. Description of the Related Art

In recent years, diagnosis was performed in various clinical scenes by observing a three-dimensional image obtained by imaging a patient. Especially, for a tubular structural organ, such as a large intestine and a bronchus or bronchi, which is observable by using an endoscope, a method for observing a region of interest, such as a lesion, has been drawing attention. In the method, plural images resembling endoscopic images (hereinafter, referred to as virtual endoscopic images), and which are virtually imaged from the inside of the tubular structure, are generated along the tubular structure from a CT image, and the virtual endoscopic images of plural positions at plural angles are successively displayed. Such image-based diagnosis using virtual endoscopic images can reduce a burden on the patient in examination, because it is not necessary to actually insert an endoscope into the patient. Further, even if an obstructed region exists in the tubular structure and the endoscope is not insertable, it is possible to display, based on the CT image, the condition of a part of the tubular structure behind the obstructed region. Therefore, there are growing expectations for the image-based diagnosis using such virtual endoscopic images.

Japanese Unexamined Patent Publication No. 2000-135215 (Patent Document 1) proposes a method in which a three-dimensional image is generated for a tube, such as a bronchus or bronchi, and a path to a target point along the tube is obtained in advance in the three-dimensional image, and a virtual endoscopic image along the path is used, as a guide image, in actual observation using an endoscope. Further, PCT Japanese Publication No. 2008-529578 (Patent Document 2) proposes a method in which a trigger is stored in such a manner to be related to a region of interest of a user. When virtual endoscopic images are successively displayed along a path as if a motion image is displayed, enhanced display is possible for the region in which the trigger has been set. A resolution, a display rate, a display time, the magnification of an image, a view angle and the like are changed based on a set viewing protocol.

SUMMARY OF THE INVENTION

Here, in observation of a tubular structure, there is a demand for improving the efficiency of image reading by reducing a display time and a calculation cost necessary to generate or display each of virtual endoscopic images at plural positions. However, in the methods disclosed in Patent Documents 1 and 2, when a virtual endoscopic image in a region of interest or in the vicinity of the region of interest is selectively generated from a three-dimensional image or displayed, a heavy work load and a long work time for selecting and setting the position of the virtual endoscopic image to be generated, or the position of the virtual endoscopic image to be displayed are necessary.

In view of the foregoing circumstances, it is an object of the present invention to provide an apparatus, a method and a program for reducing a work load and a work time in selecting and setting a position at which a virtual endoscopic image is generated from a three-dimensional image and a method for displaying the virtual endoscopic image. The position and the display method are selected and set so that only a virtual endoscopic image or images representing a region, such as a region of interest, necessary for image-based diagnosis are intensively observable.

A medical image processing apparatus according to a first invention of the present invention includes an image obtainment unit that obtains a three-dimensional image obtained by imaging a patient, a degree-of-interest setting unit that sets a relative degree of interest at each of plural positions on a path connecting the plural positions in the three-dimensional image, a discrimination condition obtainment unit that obtains a discrimination condition for identifying, based on the set degree or degrees of interest, a virtual endoscopic image or images to be generated from the three-dimensional image, and an image generation unit that generates, based on the three-dimensional image, only the virtual endoscopic image or images identified based on the discrimination condition.

A medical image processing method according to the first invention of the present invention is performed by the medical image diagnosis apparatus, and the method includes the step of obtaining a three-dimensional image obtained by imaging a patient, the step of setting a relative degree of interest at each of plural positions on a path connecting the plural positions in the three-dimensional image, the step of obtaining a discrimination condition for identifying, based on the set degree or degrees of interest, a virtual endoscopic image or images to be generated from the three-dimensional image, and the step of generating, based on the three-dimensional image, only the virtual endoscopic image or images identified based on the discrimination condition.

A medical image processing program according to the first invention of the present invention causes a computer to function as each of the aforementioned units.

A medical image processing apparatus according to a second invention of the present invention includes an image obtainment unit that obtains a three-dimensional image obtained by imaging a patient, a degree-of-interest setting unit that sets a relative degree of interest at each of plural positions on a path connecting the plural positions in the three-dimensional image, an image generation unit that generates plural virtual endoscopic images from the three-dimensional image, a discrimination condition obtainment unit that obtains a discrimination condition for identifying, based on the set degrees of interest, one or more of the generated virtual endoscopic images to be displayed, and a display control unit that displays only one or more of the generated virtual endoscopic images that have been identified based on the discrimination condition.

In the first and second inventions, the "path" may be set by using arbitrary methods. For example, when an observation object is a tubular structure, a path setting unit may set a core line connecting the center of the tubular structure, as the path. Alternatively, in the second invention, a display control unit may receive instructions about a movement direction and a movement amount input by a user while a display image at a predetermined position is displayed by using a predetermined display method. Further, the display control apparatus may display a display image at a position to which a current display position is moved by the received movement amount in the received movement direction. Further, the path setting unit may set the path by connecting display positions to each other in the order of display. In the first and second inventions, the method for setting a path may be an automatic setting method using a known technique. Alternatively, a method for setting the path by connecting positions that have been input by operations by a user at an input device may be used. Further, the automatically set path may be corrected by an operation by the user at the input device. Further, the whole path may be automatically set by an interpolation operation or the like based on a part of the path that has been set by an operation by the user at the input device.

In the first and second inventions of the present invention, the degree-of-interest setting unit may obtain a position of interest in the three-dimensional image and a degree of interest corresponding to the position of interest, and set a degree of interest by weighting in such a manner that the degree of interest is lower than the degree of interest corresponding to the position of interest as a distance from the obtained position of interest is longer. In this case, the degree-of-interest setting unit may set the degree of interest in such a manner that the degree of interest is in inverse proportion to the distance from the position of interest.

Further, the "degree of interest" represents the level of the magnitude of a request for generating or displaying a virtual endoscopic image. Further, the expression of setting "a relative degree of interest at each of positions on a path" means setting a degree of interest based on a relative level of the magnitude at each of the positions on the path with respect to each other. Further, the "position of interest" represents a localized position at which a request for generating or displaying a virtual endoscopic image is large. The position of interest may be set at an arbitrary position by using an arbitrary method. The position of interest may be located on the path, or at a position other than the path. For example, the position of interest may be a position, such as a center of gravity of a lesion extracted by using a computer-aided diagnosis technique (CAD technique), and which is included in a region of interest. Alternatively, the position of interest may be input by an operation by the user at the input device.

In the first and second inventions of the present invention, it is desirable that the path connects the plural positions within a tubular structure included in the three-dimensional image, and that the degree-of-interest setting unit sets the degree of interest based on a curvature of the path by weighting in such a manner that the degree of interest is higher as the curvature is larger.

In the first and second inventions, the expression "in such a manner that the degree of interest is lower" means weighting in such a manner that the level of a request for generating or displaying a virtual endoscopic image is lower. The expression "the degree of interest is higher" means weighting in such a manner that the level of a request for generating or displaying a virtual endoscopic image is higher. As long as these meanings are maintained, a degree of interest may be set, for example, in such a manner that the degree of interest is higher as a value representing the degree of interest is lower. Alternatively, a degree of interest may be set in such a manner that the degree of interest is higher as a value representing the degree of interest is higher.

In the first and second inventions of the present invention, the discrimination condition may be a threshold condition for identifying the virtual endoscopic image or images.

In the first and second inventions of the present invention, the discrimination condition obtainment unit may obtain the number of a virtual endoscopic image or images displayable at a predetermined display speed within a predetermined display time, and set a threshold to identify a virtual endoscopic image or images corresponding to the obtained number of a virtual endoscopic image or images.

In the first and second inventions of the present invention, the virtual endoscopic image may be a virtual bronchial endoscopic image, and the position of interest may be a branching part of a bronchus or bronchi included in the three-dimensional image. Further, the virtual endoscopic image may be a virtual laparoscopic endoscopic image.

The medical image processing apparatus in the first invention of the present invention sets a relative degree of interest at each of plural positions on a path connecting the plural positions in the three-dimensional image, obtains a discrimination condition for identifying, based on the set degree or degrees of interest, a virtual endoscopic image or images to be generated from the three-dimensional image, and generates, based on the three-dimensional image, only the virtual endoscopic image or images that have been identified based on the discrimination condition. Therefore, it is possible to easily identify, based on the relative degree or degrees of interest set for the path, the virtual endoscopic image or images to be generated from the three-dimensional image only by setting the discrimination condition. Hence, a work time and a work load for selectively generating a virtual endoscopic image or images are reduced, and that can assist in improving the efficiency of image reading.

The medical image processing apparatus in the second invention of the present invention sets a relative degree of interest at each of plural positions on a path connecting the plural positions in the three-dimensional image, obtains a discrimination condition for identifying, based on the set degrees of interest, one or more of virtual endoscopic images to be displayed, and displays only one or more of the virtual endoscopic images that have been identified based on the discrimination condition. Therefore, it is possible to easily identify, based on the relative degrees of interest that have been set for the path, a virtual endoscopic image or images to be displayed from the three-dimensional image only by setting the discrimination condition. Hence, a work time and a work load for selectively displaying a virtual endoscopic image or images are reduced, and that can assist in improving the efficiency of image reading.

DESCRIPTION OF THE PREFERRED EMBODIMENTS

Hereinafter, embodiments of the present invention will be described by using a case of performing image-based diagnosis by a medical image representing the large intestine of a human body, as an example.

Figure 1:
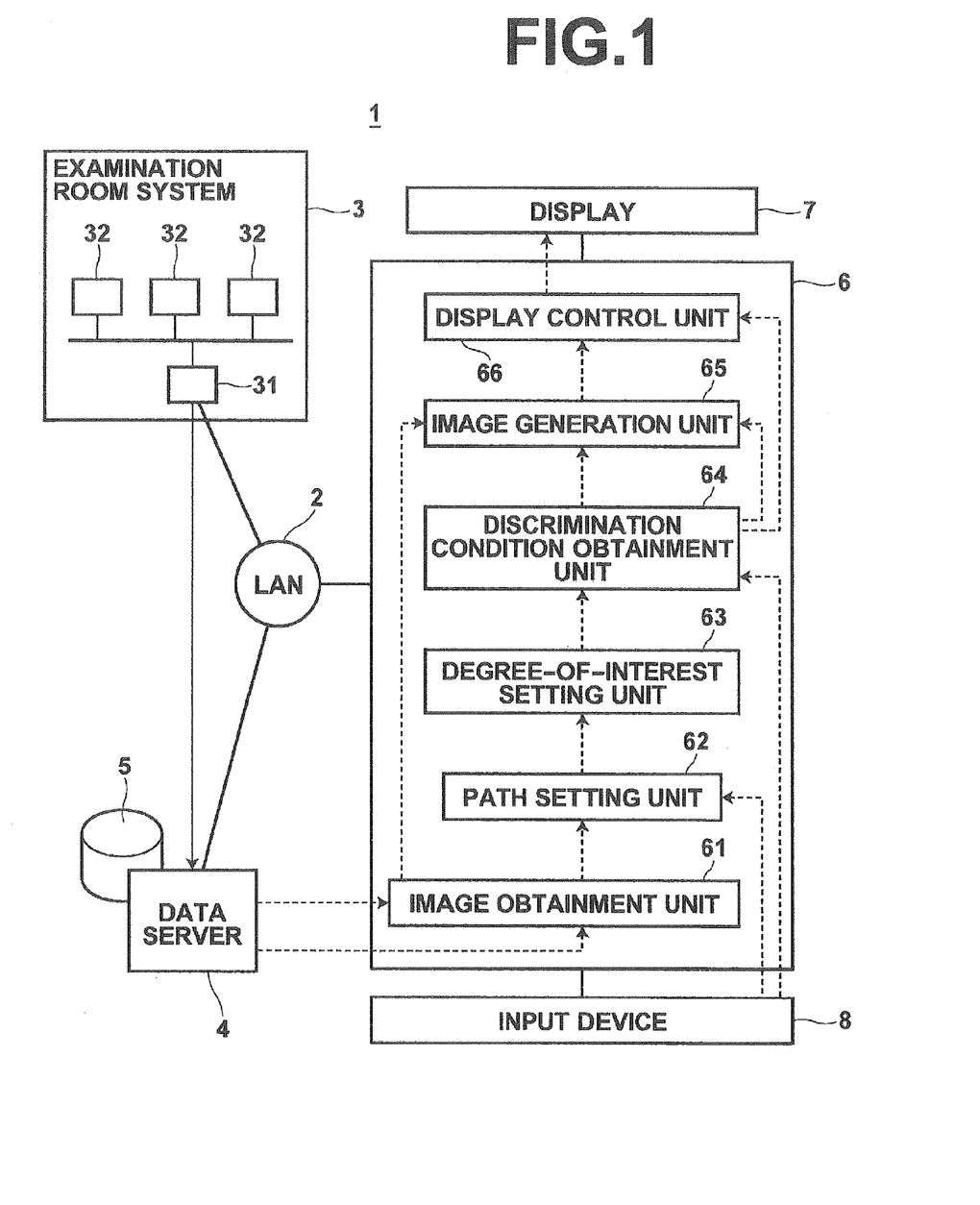
FIG. 1 is a schematic block diagram illustrating configuration and a flow of processing for achieving medical image processing functions according to a first embodiment.

FIG. 1 is a schematic diagram illustrating the configuration of a medical image processing system 1 including a medical image processing apparatus 6 according to an embodiment of the present invention. The medical image processing system 1 includes an examination room system 3, a data server 4 and a workstation (WS) 6 for diagnosis, which are connected to each other through a local area network (LAN) 2.

The examination room system 3 includes various kinds of modality 32 for imaging a subject to be examined and an examination room workstation (WS) 31 for checking or adjusting images output from each of the modalities. As the modalities 32, a CT (Computed Tomography) apparatus and an MRI (Magnetic Resonance Imaging) apparatus, which can obtain three-dimensional image V, are provided. Further, an ultrasonic diagnosis apparatus or the like is provided. Both of the CT (Computed Tomography) apparatus and the MRI (Magnetic Resonance Imaging) apparatus of the modalities 32 are based on DICOM (Digital Imaging and Communication in Medicine) standard, and output obtained volume data, as a DICOM file, by attaching supplementary information to the volume data.

The file that has been output from the modality 32 is transferred to the data server 4 by the examination room WS 31. The data server 4 is a relatively high performance computer including a high performance processor and a large capacity memory, and a software program that provides a database management server (DBMS: Database Management Server) function has been installed in the computer. The program is stored in a storage, and loaded into the memory at boot-up, and executed by the processor. The data server 4 stores the file transferred from the examination room WS 31 in a large capacity storage 5. Further, the data server 4 selects, based on a retrieval request from the WS 6 for diagnosis, a file satisfying the retrieval condition from plural files stored in the large capacity storage 5, and sends the selected file to the WS 6 for diagnosis. In the embodiment of the present invention, three-dimensional image data representing the abdomen of a human body including the large intestine have been generated by scanning the human body, as a subject to be examined, in the direction of the body axis by a CT apparatus, and stored in the data server 4.

The WS 6 for diagnosis is a general-purpose workstation including a standard processor, a memory and a storage, and in which an image processing program for assisting on diagnosis has been installed. The image processing program is installed in the WS 6 for diagnosis by download from a recording medium, such as a DVD, or by download from a server computer in a network. Further, a display 7 and an input device 8, such as a mouse and a keyboard, are connected to the WS 6 for diagnosis.

The image processing program installed in the WS 6 for diagnosis is composed of program module groups for realizing various functions, which include a program module group for realizing an image processing function. These programs are stored in a storage, and loaded into the memory at boot-up, and executed by the processor. Accordingly, the WS 6 for diagnosis operates as an image obtainment unit 61 that obtains three-dimensional image V, a path setting unit 62 that sets a path connecting plural positions in three-dimensional image V, a degree-of-interest setting unit 63 that sets a relative degree of interest at each position on the path, a discrimination condition obtainment unit 64 that obtains a discrimination condition for identifying, based on the degree or degrees of interest, a virtual endoscopic image or images to be generated from three-dimensional image V, an image generation unit 65 that generates only the virtual endoscopic image or images identified based on the discrimination condition, and a display control unit 66 that displays the virtual endoscopic image or images.

Each unit of the WS 6 for diagnosis will be described in detail.

Before processing in the embodiment of the present invention is performed, the abdomen of a subject is imaged by a CT apparatus or the like in an examination on the large intestine. Supplementary information is attached to three-dimensional image V (volume data) obtained by imaging, and three-dimensional image data V, as a DICOM file, are transferred to the data server 4, and stored in the large capacity storage 5.

First, when an image processing function for the large intestine is selected in an initial screen, and an identification number of a patient, an examination number or the like is input in a predetermined input screen, the image obtainment unit 61 sends the input information to the data server 4, and requests retrieval and transfer of a file stored in the large capacity storage 5. The data server 4, which has received the request, retrieves the file from the large capacity storage 5, and transfers the requested file to the image obtainment unit 61. The image obtainment unit 61 obtains three-dimensional image V included in the file transferred from the data server 4, and stores three-dimensional image V in the memory.

Figure 2:
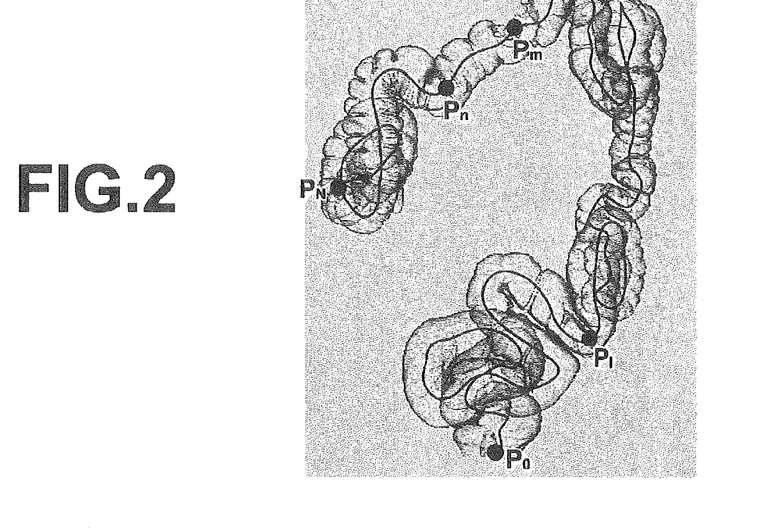
FIG. 2 is a schematic diagram illustrating a path of a large intestine and positions of interest set for a three-dimensional medical image in the first embodiment.

The path setting unit 62 sets a path connecting plural positions in obtained three-dimensional image V. Here, the path setting unit 62 extracts a large intestine region from three-dimensional image V, and performs core line extraction processing on the extracted large intestine region. Further, the path setting unit 62 displays the large intestine region and the core line extracted from three-dimensional image V on a display 7. The path setting unit 62 receives selection of one of end points of the core line of the large intestine, as a start point of the path, by an operation by a user using a mouse or the like. Accordingly, path P along the core line of the large intestine from end point $P_0$, which is the selected start point, to the other endpoint $P_N$ is set. FIG. 2 is a schematic diagram illustrating path P of the large intestine from start point $P_0$ to the terminal point $P_N$, which has been set for three-dimensional image V.

In the processing for extracting the large intestine, first, processing for dividing each of axial tomographic images obtained from the three-dimensional medical image, and which represent slice planes perpendicular to the body axis (axial section), into a region in the body and a region outside the body with respect to the surface of the body is performed by using a known technique. As specific examples, there are a method in which binarization processing is performed on an input axial tomographic image, and an outline is extracted by performing outline extraction processing, and a region inside the extracted outline is extracted, as a region in the body (human body), and the like. Next, binarization processing using a threshold is performed on the region in the body, and a candidate of the large intestine region is extracted from each of the axial tomographic images. Specifically, since air is present in the tube of the large intestine, binarization processing is performed by setting a threshold corresponding to a CT value of air, and an air region in the body is extracted from each of the axial tomographic images. Finally, only a part in which the extracted air region in the body in each of the axial tomographic images is connected to each other is extracted as the large intestine region.

In processing for extracting the core line, the core line passing through a central part of the tube of the large intestine is extracted from the extracted large intestine region by using a known technique. As specific examples, there are a method in which three-dimensional thinning processing is performed on a binary image representing the large intestine region that has been obtained during extraction of the large intestine by extracting only a part in which air regions in the body are connected to each other (please refer to Japanese Unexamined Patent Publication No. 2004-283373 and the like), and the like.

Here, a user interface for manually correcting the result of extraction of the large intestine region and the core line may be further provided. As a specific example, there is an interface in which the extracted large intestine region and the core line in each of the axial tomographic images are displayed with emphasis, and a user corrects the result of extraction of the large intestine region and the core line (in an image, a point representing the core line) in each of the axial tomographic images by operating a mouse or the like, if the extraction result is wrong.

In the embodiment of the present invention, the degree-of-interest setting unit 63 sets a relative degree of interest at each of plural positions on path P set by the path setting unit 62, and which connects the plural positions in the three-dimensional image.

First, the degree-of-interest setting unit 63 sets one or more positions of interest $P_q$ in the three-dimensional image. FIG. 2 illustrates an example in which positions with q=l, m, n are set as positions of interest. In FIG. 2, l, m and n are natural numbers less than or equal to N. In the embodiment of the present invention, the large intestine region and path P (the core line of the large intestine) are displayed on a display, as illustrated in FIG. 2, and a selected position or positions of interest are obtained by selection of a desirable point or points on path P by a user using a mouse or the like. Further, a degree or degrees of interest that have been input by the user using a keyboard or the like, and which correspond to the position or positions of interest, respectively, are obtained. Then, the degree-of-interest setting unit 63 stores the obtained position or positions of interest and the degree or degrees of interest in such a manner to be related to each other. Here, it is assumed that degrees of interest of al=0.7, am=0.9 and an=0.6 are set as the degrees of interest at $P_l$, $P_m$ and $P_n$, respectively. In the embodiment of the present invention, start point $P_0$ and terminal point $P_N$ of path P are automatically set as positions of interest, and predetermined values of a0=0.8 and aN=0.8, as degrees of interest, are related to start point $P_0$ and terminal point $P_N$, respectively.

Then, the degree-of-interest setting unit 63 obtains positions of interest (in this case, $P_0$, $P_l$, $P_m$, $P_n$ and $P_N$) and degrees of interest of a0, al, am, an and aN corresponding to the positions of interest. Further, the degree-of-interest setting unit 63 sets a degree of interest by weighting in such a manner that the degree of interest is lower than the degree of interest corresponding to the position of interest as a distance from the obtained position of interest is longer.

In the embodiment of the present invention, the degree-of-interest setting unit 63 sets a degree of interest, based on the following expression (1), in such a manner that the degree of interest is in inverse proportion to a distance from the position of interest. Here, p represents an arbitrary point on the path. Further, $P_q$ and aq (0≤q≤N) represent a position of interest and a degree of interest corresponding to the position of interest. Here, each of a relative degree or degrees of interest F(p) for the whole path is calculated by using the following expression (1). In expression (1), Q is a set of positions of interest. Further, the present invention is not limited to the embodiment of the present invention. Even if a position of interest is not located on the path, as long as the coordinate of the position of interest and a degree of interest corresponding to the position of interest are obtainable, it is possible to calculate a relative degree of interest at each position on the path by using the following expression (1). In the following expression (1), $P_q$ and aq represent a position of interest with a shortest distance from position p and its degree of interest, respectively:

$$F(p)=aq/[1+(p-P_q)^2] \qquad (1)$$

Further, in the embodiment of the present invention, the degree-of-interest setting unit 63 sets the degree of interest based on the curvature of the path further by weighting in such a manner that the degree of interest is higher as the curvature of the path is larger. Specifically, the degree-of-interest setting unit 63 calculates a curvature at each position on path P, and sets, based on the curvature, degree of interest Fc(p) for each of the positions on path P in such a manner that the degree of interest is higher as the curvature is larger. Then, the degree-of-interest setting unit 63 further adds degree of interest Fc(p) based on the curvature by weighted addition to the aforementioned degree of interest F(p) to obtain relative degree of interest F(p)'(=F(p)+αFc(p), where α is a predetermined weighting coefficient) for the whole path. Here, it is assumed that weighting coefficient α has been set in such a manner that the product of the maximum value of Fc(p) and α is less than or equal to 0.5 so that the maximum value of degree of interest Fc(p) based on the curvature is lower than the maximum value of degree of interest F(p) related to the position of interest.

Figure 3:
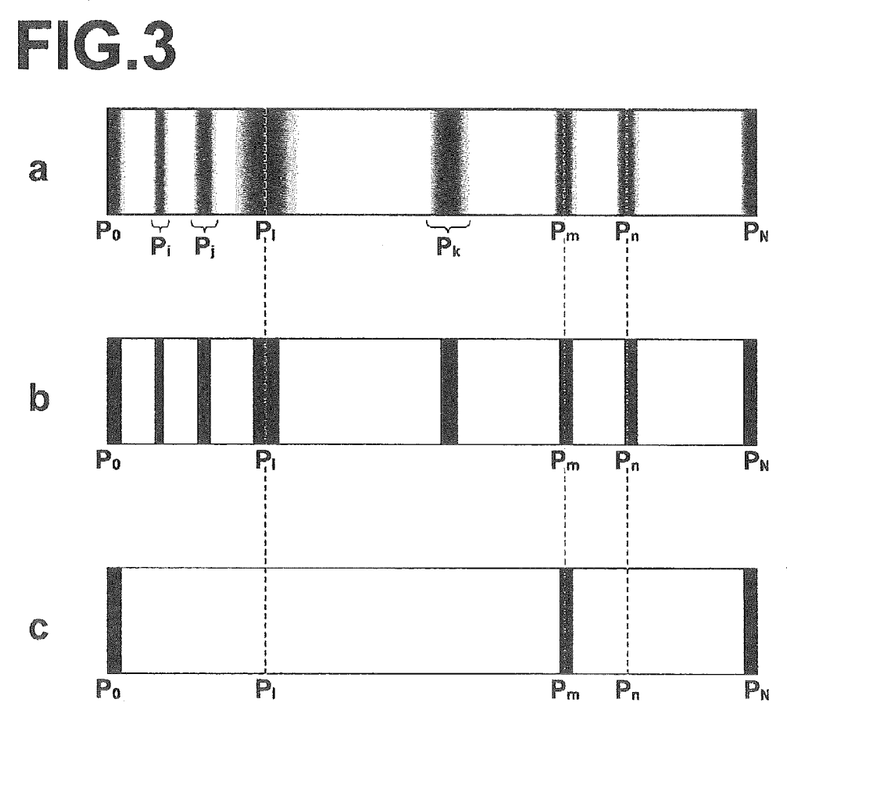
FIG. 3 is a schematic diagram illustrating an example of a path of a large intestine and degrees of interest in the first embodiment.

FIG. 3, Section a is a diagram illustrating an image representing degree of interest F(p)', which has been obtained as described above, by grayscale in such a manner that the image is darker as the degree of interest is higher. In the example of FIG. 3, Section a, the degrees of interest are set in such a manner that the degree of interest is lower as a distance from position of interest $P_0$, $P_l$, $P_m$, $P_n$ and $P_N$ is longer. Relatively high degrees of interest are set for positions included in the ranges represented by $P_i$, $P_j$ and $P_k$ based on the curvatures.

The discrimination condition obtainment unit 64 obtains a discrimination condition for identifying, based on the degree or degrees of interest, a virtual endoscopic image or images to be generated from a three-dimensional image. In the embodiment of the present invention, the discrimination condition is a threshold condition for identifying a virtual endoscopic image or images to be generated. A threshold defined in the threshold condition may be, for example, a default value, which has been set in advance, or a value set by a user or the like by using the input device 8. Further, in the medical image processing apparatus according to the embodiment of the present invention, the discrimination condition (a threshold in this case) is changeable by a input by the user or the like at the input device 8. The discrimination condition obtainment unit 64 obtains, based on the change in the discrimination condition, a discrimination condition after change.

In the embodiment of the present invention, the image generation unit 65 generates, based on three-dimensional image V, only a virtual endoscopic image or images identified based on the discrimination condition. Specifically, the image generation unit 65 generates, based on the threshold defined in the discrimination condition, only a virtual endoscopic image or images viewed from a viewpoint or viewpoints corresponding to a degree of interest or degrees of interest that are higher than the threshold. Accordingly, virtual endoscopic image I, which is viewed from a position with a degree of interest that is higher than the threshold, is generated from three-dimensional image V. As a specific method of center projection, for example, a known volume rendering method may be used. Further, a viewing angle (the range of view lines) and the center of a viewing field (the center of a projection direction) may be given in advance by a boot parameter of a setting file or a program, an input by a user, or the like.

Meanwhile, FIG. 3, Sections b and c illustrate identified positions of interest of the positions of interest along the path illustrated in FIG. 3, Section a. The identified positions of interest based on different discrimination conditions are illustrated in black in FIG. 3, Sections b and c, respectively. For example, when a user wants to generate a minimum number of virtual endoscopic images, if threshold T is set, for example, at 0.75 as illustrated in FIG. 3, Section c, it is possible to generate only a virtual endoscopic image at each position included in black areas in the vicinities of $P_0$, $P_m$ and $P_N$, which satisfy the discrimination condition that degree of interest $F(p)'$ is 0.75 or higher. Further, when a user wants to observe virtual endoscopic images in a wide range to some extent, if threshold T is set, for example, at 0.45 as illustrated in FIG. 3, Section b, it is possible to generate a virtual endoscopic image at each position included in black areas in the vicinity of $P_0$, $P_l$, $P_m$, $P_n$ and $P_N$.

The display control unit 66 displays the generated virtual endoscopic image or images on the display of the image processing workstation 3.

Figure 4:
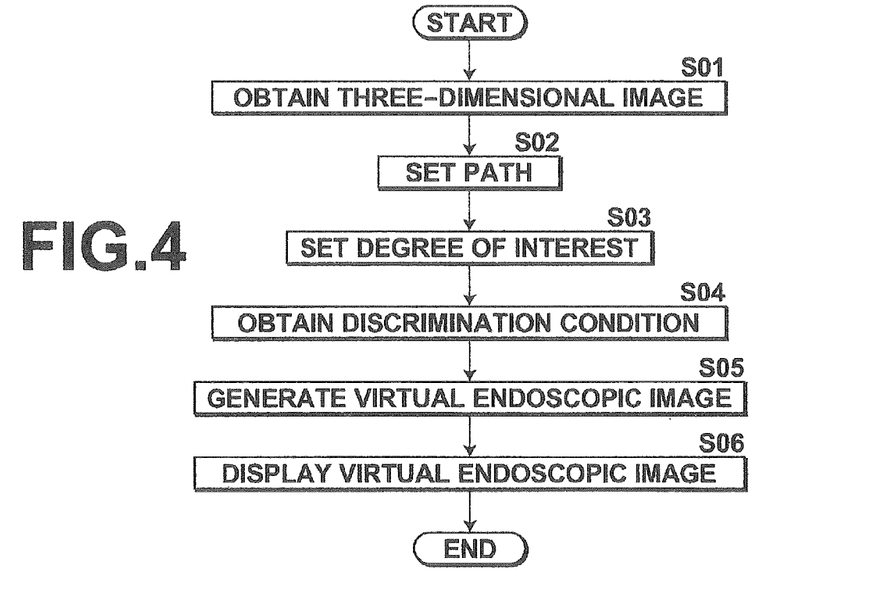
FIG. 4 is a flow chart illustrating a flow of medical image processing in the first embodiment.

FIG. 4 is a flow chart illustrating the flow of medical image processing according to the first embodiment of the present invention. The flow of medical image processing in the first embodiment will be described with reference to FIG. 4.

First, the image obtainment unit 61 obtains three-dimensional image V included in a file transferred from the data server 4, and stores three-dimensional image V in a memory (S01). Next, the path setting unit 62 sets path P along the large intestine in the three-dimensional image (S02). Then, the degree-of-interest setting unit 63 sets positions of interest $P_0$, $P_l$, $P_n$ and $P_N$ in path P and degrees of interest corresponding to them. The degree-of-interest setting unit 63 also calculates, based on expression (1), degree of interest $F(p)$ at each position on the path, and further calculates, based on the curvature of the path, degree of interest $Fc(p)$ at each of the positions on the path. The degree-of-interest setting unit 63 adds these together by weighted addition, and sets degree of interest $F(p)$ at each of the positions, as illustrated in FIG. 3, Section a (S03).

Next, the discrimination condition obtainment unit 64 obtains a discrimination condition (S04). Then, the image generation unit 65 generates each virtual endoscopic image I identified based on the discrimination condition from three-dimensional image V (S05). Then, the display control unit 66 displays each virtual endoscopic image I, which has been generated, on a display (S06).

As described, the first embodiment of the present invention sets a relative degree of interest at each of plural positions on a path connecting the plural positions in the three-dimensional image, obtains a discrimination condition for identifying, based on the set degree or degrees of interest, a virtual endoscopic image or images to be generated from the three-dimensional image, and generates, based on the three-dimensional image, only the virtual endoscopic image or images identified based on the discrimination condition. Therefore, it is possible to easily identify, based on the relative degree or degrees of interest set for the path, the virtual endoscopic image or images to be generated from the three-dimensional image only by setting the discrimination condition. Hence, a work time and a work load for selectively generating a virtual endoscopic image or images are reduced, and that can assist in improving the efficiency of image reading.

In the first embodiment, the discrimination condition for identifying "a virtual endoscopic image or images to be generated" is used. Alternatively, as in the second embodiment, the discrimination condition for identifying "a virtual endoscopic image or images to be displayed" may be used. The second embodiment differs from the first embodiment only in that the discrimination condition identifies a virtual endoscopic image or images to be displayed based on the set degree or degrees of interest, and in that the image generation unit 65 generates, based on a three-dimensional image, virtual endoscopic images for the whole tubular structure or a part of the tubular structure, and in that the display control unit 66 displays only one or more of the virtual endoscopic images generated by the display control unit 66 that have been identified based on the discrimination condition. Next, a flow of processing in the second embodiment will be described with reference to the flow chart illustrated in FIG. 4. The different points from the first embodiment will be mainly described. Explanations will be omitted for the function of each function block and processing that are the same as those of the first embodiment.

In the flow of medical image processing in the second embodiment, S01 through S04 are the same as the first embodiment. Then, instead of processing in S05, the image generation unit 65 in the second embodiment generates, along the path (core line), a predetermined number of virtual endoscopic image or images I with a predetermined interval from three-dimensional image V (S05'). Then, instead of processing in S06, the display control unit 66 in the second embodiment displays only one or more of generated virtual endoscopic images I that have been identified based on the discrimination condition on a display (S06').

The second embodiment sets a relative degree of interest at each of plural positions on a path connecting the plural positions in the three-dimensional image, obtains a discrimination condition for identifying, based on the set degrees of interest, a virtual endoscopic image or images to be displayed, and displays only one or more of the generated virtual endoscopic images that have been identified based on the discrimination condition. Therefore, it is possible to easily identify, based on the relative degrees of interest that have been set for the path, the virtual endoscopic image or images to be displayed from the three-dimensional image only by setting the discrimination condition. Hence, a work time and a work load for selectively displaying a virtual endoscopic image or images are reduced, and that can assist in improving the efficiency of image reading.

According to the first and second embodiments, the degree-of-interest setting unit 63 obtains a position of interest and a degree of interest corresponding to the position of interest, and sets a degree of interest by weighting in such a manner that the degree of interest is lower than the degree of interest corresponding to the position of interest as a distance from the obtained position of interest is longer. Therefore, it is possible to appropriately set not only the degree of interest at the position of interest, but also degrees of interest in the vicinity of the position of interest based on the level of interest corresponding to the position of interest. Therefore, it is possible to generate or display, based on the level of interest, many virtual endoscopic images in the vicinity of the position of interest, and to omit generation and display of a virtual endoscopic image in a region away from the position of interest. In other words, it is possible to appropriately satisfy a request by a user to intensively observe the position of interest by observing plural positions in the vicinity of the position of interest, and to automatically set a degree or degrees of interest for a region in the vicinity of the position of interest if the position of interest and the degree of interest at the position of interest are obtained. Therefore, a work time and a work load for selectively generating or displaying a virtual endoscopic image or images are appropriately reducible.

According to the first and second embodiments, the degree-of-interest setting unit sets the degree of interest by weighting in such a manner that the degree of interest is in inverse proportion to the distance from the position of interest. Therefore, it is possible to easily set a degree or degrees of interest based on the position of interest.

According to the first and second embodiments, the discrimination condition is a threshold condition. Therefore, it is possible to adjust the number of a virtual endoscopic image or images to be generated or the number of a virtual endoscopic image or images to be displayed only by adjusting a threshold. Therefore, a work time and a work load for selectively generating or displaying the virtual endoscopic image or images are very appropriately reducible.

Further, according to the first and second embodiments, the path connects plural positions within a tubular structure included in the three-dimensional image. Further, the degree-of-interest setting unit sets, based on a curvature of the path, the degree of interest by weighting in such a manner that the degree of interest is higher as the curvature is larger. Therefore, it is possible to set the degree or degrees of interest to satisfy a request for intensively observing a region with a large curvature, and to easily and appropriately generate or display a virtual endoscopic image at a position based on its curvature. Especially, when the virtual endoscopic image is a virtual laparoscopic endoscopic image, it is possible to set a degree of interest to appropriately satisfy a request at a medical treatment site for observing a curved or bent region of the large intestine. Therefore, it is possible to easily and appropriately generate or display a virtual endoscopic image of the curved or bent region of the large intestine.

According to the first and second embodiments, when the discrimination condition has been changed, the display control unit 66 displays only a virtual endoscopic image or images based on the discrimination condition after change. Therefore, it is possible to flexibly satisfy the request by the user. Further, it is possible to easily adjust a generation amount and a display amount of the virtual endoscopic image or images.

Here, the first embodiment and the second embodiment may be combined together, and the image generation unit 65 may generate only a virtual endoscopic image or images identified based on a discrimination condition, and the display control unit 66 may display only the virtual endoscopic image or images identified based on a discrimination condition. In this case, the discrimination conditions may include a condition for identifying a virtual endoscopic image or images to be generated and a condition for identifying a virtual endoscopic image or images to be displayed, respectively.

As a third embodiment, an application example of the degree-of-interest setting unit 63 of the first embodiment will be described with reference to FIG. 5 and FIG. 6. When the tubular structure has a branching part, the degree-of-interest setting unit 63 in the third embodiment sets a position of interest in the branching part. The function of each unit and processing other than processing for setting a degree of interest by the degree-of-interest setting unit 63 are the same as the first embodiment. Therefore, the different point between the first embodiment and the third embodiment will be mainly described. Explanations will be omitted for the function and processing that are the same as those of the first embodiment.

Figure 5:
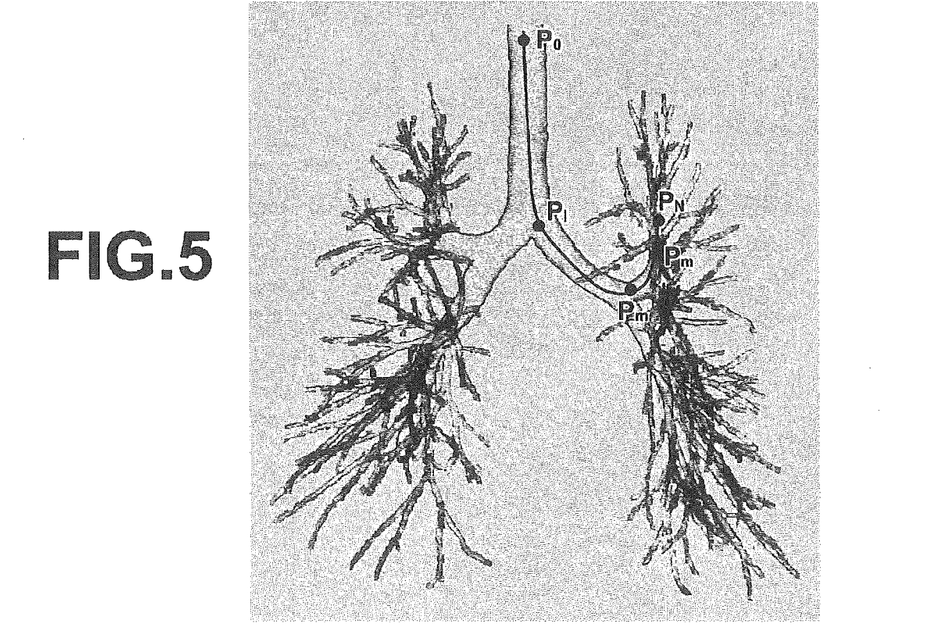
FIG. 5 is a schematic diagram illustrating a path of bronchi and positions of interest set for a three-dimensional medical image in a third embodiment.

FIG. 5 is a diagram illustrating an example in which branching positions of branching parts automatically obtained by using a known method are set as positions of interest $P_l$, $P_m$ and $P_n$ for bronchi, which are a tubular structure having branching parts. FIG. 6 is a diagram representing degrees of interest corresponding to FIG. 5 by grayscale in such a manner to be darker as the degree of interest is higher.

Figure 6:
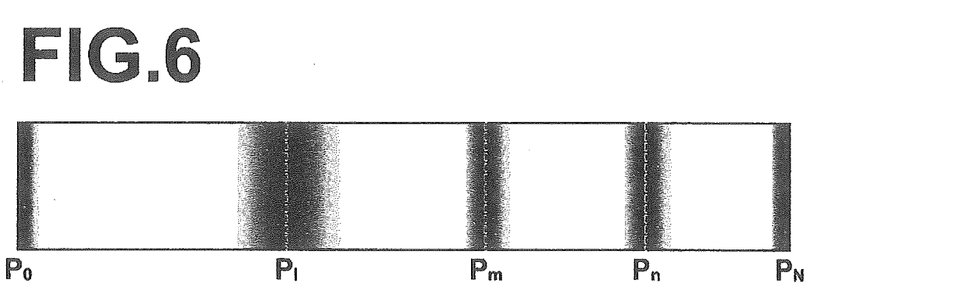
FIG. 6 is a schematic diagram illustrating an example of a path of bronchi and degrees of interest in the third embodiment.

As illustrated in FIG. 5 and FIG. 6, the degree-of-interest setting unit 63 in the third embodiment obtains positions of interest (in this case, $P_l$, $P_m$ and $P_n$) representing branching parts and degrees of interest corresponding to the positions of interest, and sets a degree of interest by weighting in such a manner that the degree of interest is lower than a degree of interest corresponding to the position of interest as a distance from the obtained position of interest is longer. Here, start point $P_0$ and terminal point $P_N$ of the path are automatically set as positions of interest in a similar manner to the first embodiment. The degree-of-interest setting unit 63 calculates, based on the following expression (2), a degree of interest corresponding to the position of interest, and sets the degree of interest, as illustrated in FIG. 6. In expression (2), Q: a set of a position or positions of interest on the path (in this case, a set of branching parts of the bronchi on the path), and:

$$F(p)=1/[1+\min_{P_q \in Q}(p-P_q)^2] \qquad (2).$$

In the third embodiment, the virtual endoscopic image is a virtual bronchial endoscopic image, and the position of interest is a branching part of a bronchus or bronchi included in the three-dimensional image. Therefore, it is possible to appropriately and easily generate or display a virtual endoscopic image or images to satisfy a request by a user who wants to check a branching position for a bronchus or bronchi.

In the third embodiment, as the method for obtaining the position of a branching part, as a position of interest, a position that has been manually input may be obtained as the position of interest. Alternatively, a position that has been judged as a branching part by using a known method may be automatically obtained as the position of interest.

In each of the aforementioned embodiments, the degree-of-interest setting unit may use, as a relative degree of interest, only one of a degree of interest based on a position of interest, a degree of interest based on a curvature and a degree of interest based on a branching part. Alternatively, the degree-of-interest setting unit may use, as the relative degree of interest, an arbitrary combination of two or more of a degree of interest based on a position of interest, a degree of interest based on a curvature and a degree of interest based on a branching part. Further, weighting may be performed on the relative degree of interest in each of the embodiments by using another degree of interest or other degrees of interest. Further, a relative degree of interest may be set by combining plural degrees of interest, such as a degree of interest based on a position of interest, a degree of interest based on a curvature and a degree of interest based on a branching part, by using an arbitrary method as long as the relative degree of interest is settable for the path. Further, instead of expression (1), an arbitrary expression in which the degree of interest is lower as a distance from the position of interest is longer may be used. Further, instead of expression (2), an arbitrary expression in which the degree of interest is lower as a distance from the branching part is longer may be used.

Figure 7:
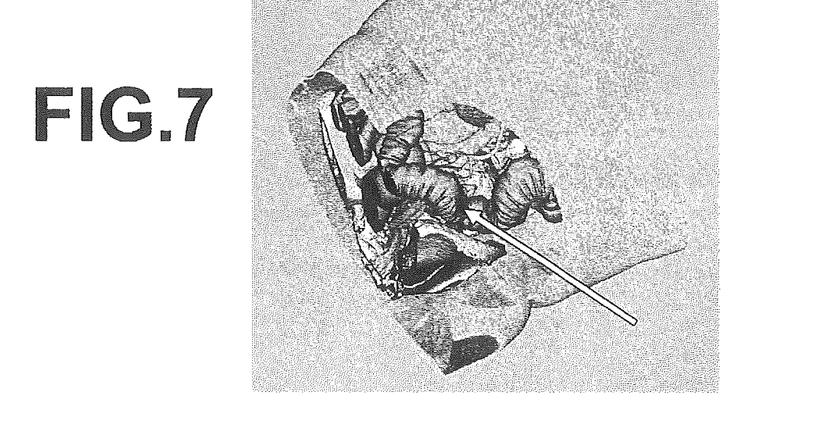
FIG. 7 is a diagram for explaining a modified example of setting a path.

It is not necessary that a path in each of the embodiments is set along a tubular structure by manual or automatic extraction processing, as described above. For example, as illustrated in FIG. 7, in the medical image processing apparatus, the display control unit 66 may generate a display image at an arbitrary predetermined initial position by using a predetermined display method. While the display image is displayed, the display control unit 66 may display movement buttons for up, down, left, right, front and back directions. The display control unit 66 may display, based the kind of the movement button and the number of a click or clicks of a mouse or the like by the user, a new display image at a position moved in the input movement direction by a predetermined movement amount corresponding to the number of the click or clicks. Further, the path setting unit 62 may store information for identifying positions of display images (display positions), and set a path by connecting the display positions in the order of display. Even if an arbitrary path that is not related to a structure included in three-dimensional image V is set in this manner, if a position of interest, as indicated by an arrow in FIG. 7, and a corresponding degree of interest are obtainable, it is possible to achieve a similar effect to each of the aforementioned embodiments by setting a degree of interest, based on expression (1), in such a manner that the degree of interest is lower as a distance from the position of interest is longer.

In each of the embodiments, a region of interest, such as a lesion region, may be extracted by using a known computer-aided diagnosis technique (CAD technique), and a position representing the region of interest (for example, the center of gravity of the region of interest), such as a point included in the extracted region of interest, may be obtained as a position of interest.

In each of the embodiments, the discrimination condition obtainment unit 64 may obtain the number of a virtual endoscopic image or images to be generated or the number of a virtual endoscopic image or images to be displayed. Further, the discrimination condition obtainment unit 64 may automatically set a discrimination condition based on the obtained number of a virtual endoscopic image or images to be generated or the obtained number of a virtual endoscopic image or images to be displayed. When at least the number of a virtual endoscopic image or images to be generated or the number of a virtual endoscopic image or images to be displayed is obtained, it is possible to appropriately and easily identify only a virtual endoscopic image or images with a high degree or degrees of interest within the range of the obtained number of a virtual endoscopic image or images to be generated or the obtained number of a virtual endoscopic image or images to be displayed. Further, it is possible to generate or display the identified virtual endoscopic image or images. For example, the discrimination condition obtainment unit 64 may obtain the number of a virtual endoscopic image or images displayable at a predetermined display speed within a predetermined display time, and set a threshold to identify a virtual endoscopic image or images corresponding to the obtained number of a virtual endoscopic image or images. In this case, it is possible to further reduce the work of setting the discrimination condition, and it is possible to easily identify a virtual endoscopic image or images displayable at a predetermined display speed within a predetermined display time.

In the first embodiment, discrimination condition obtainment processing may be performed any time as long as the processing is performed before image generation processing. In the second embodiment, discrimination condition obtainment processing may be performed any time as long as the processing is performed before display control processing.

Further, each of the aforementioned embodiments may be combined in an arbitrary manner.

Each of the aforementioned embodiments is only an example, and none of the descriptions should be used to construe the technical scope of the present invention in a limited manner. Further, the system configuration, the hardware configuration, the flow of processing, the module configuration, user interface, the specific contents of processing and the like in the aforementioned embodiments may be modified in various manners without departing from the spirit of the present invention, and such modifications remain within the technical scope of the present invention.

Further, the configuration illustrated in FIG. 1 may include plural image processing workstations 3, and processing may be shared by the workstations.

What is claimed is:

1. A medical image processing apparatus comprising:
an image obtainment unit that is configured to obtain a three-dimensional image obtained by imaging an area of a patient body;
an extraction unit that is configured to extract, from the three-dimensional image, an organ of interest within the imaged area of the patient body;
a degree-of-interest setting unit that is configured to
set a relative degree of interest at each of a plurality of positions on a path connecting the plurality of positions in the organ of interest;
a discrimination condition obtainment unit that is configured to obtain a discrimination condition for identifying, based on the set degree or degrees of interest, whether or not to generate a virtual endoscopic image corresponding to each position on the path from the three-dimensional image; and
an image generation unit that is configured to identify each position on the path which has a degree of interest greater than or equal to a threshold value based on the discrimination condition and generate, based on the three-dimensional image, only the virtual endoscopic image or images viewed from viewpoints corresponding to the identified positions, respectively.

2. The medical image processing apparatus, as defined in claim 1, wherein the degree-of-interest setting unit is configured to obtain a position of interest in the three-dimensional image and a degree of interest corresponding to the position of interest, and set a degree of interest by weighting in such a manner that the degree of interest is lower than the degree of interest corresponding to the position of interest as a distance from the obtained position of interest is longer.

3. The medical image processing apparatus, as defined in claim 2, wherein the degree-of-interest setting unit is configured to set the degree of interest in such a manner that the degree of interest is in inverse proportion to the distance from the position of interest.

4. The medical image processing apparatus, as defined in claim 1, wherein the path connects the plurality of positions within a tubular structure included in the three-dimensional image, and
wherein the degree-of-interest setting unit is configured to set the degree of interest based on a curvature of the path by weighting in such a manner that the degree of interest is higher as the curvature is larger.

5. The medical image processing apparatus, as defined in claim 1, wherein the discrimination condition obtainment unit is configured to obtain the number of a virtual endoscopic image or images displayable at a predetermined display speed within a predetermined display time, and set a threshold of the threshold condition to identify a position of the path corresponding to the obtained number of a virtual endoscopic image or images.

6. The medical image processing apparatus, as defined in claim 1, wherein the virtual endoscopic image comprises a virtual bronchial endoscopic image, and
wherein the position of interest comprises a branching part of a bronchus or bronchi included in the three-dimensional image.

7. The medical image processing apparatus, as defined in claim 1, wherein the virtual endoscopic image comprises a virtual laparoscopic endoscopic image.

8. A medical image processing apparatus comprising:
an image obtainment unit that is configured to obtain a three-dimensional image obtained by imaging an area of a patient body;
an extraction unit that is configured to extract, from the three-dimensional image, an i organ of interest within the imaged area of the patient body;
a degree-of-interest setting unit that is configured to
set a relative degree of interest at each of a plurality of positions on a path connecting the plurality of positions in the organ of interest;
an image generation unit that is configured to generate a plurality of virtual endoscopic images viewed from viewpoints corresponding to predetermined positions on the path from the three-dimensional image;
a discrimination condition obtainment unit that obtains a discrimination condition for identifying, based on the set degrees of interest, whether to display the generated virtual endoscopic images corresponding to each position on the path; and
a display control unit that is configured to identify each position on the path which has a degree of interest greater than or equal to a threshold value based on the discrimination condition and display only one or more of the generated virtual endoscopic images corresponding to the identified positions, respectively.

9. The medical image processing apparatus, as defined in claim 8, wherein the degree-of-interest setting unit is configured to obtain a position of interest in the three-dimensional image and a degree of interest corresponding to the position of interest, and set a degree of interest by weighting in such a manner that the degree of interest is lower than the degree of interest corresponding to the position of interest as a distance from the obtained position of interest is longer.

10. The medical image processing apparatus, as defined in claim 9, wherein the degree-of-interest setting unit is configured to set the degree of interest in such a manner that the degree of interest is in inverse proportion to the distance from the position of interest.

11. The medical image processing apparatus, as defined in claim 8, wherein the path connects the plurality of positions within a tubular structure included in the three-dimensional image, and
wherein the degree-of-interest setting unit is configured to set the degree of interest based on a curvature of the path by weighting in such a manner that the degree of interest is higher as the curvature is larger.

12. The medical image processing apparatus, as defined in claim 8, wherein the discrimination condition obtainment unit is configured to obtain the number of a virtual endoscopic image or images displayable at a predetermined display speed within a predetermined display time, and set a threshold of the threshold condition to identify position of the path corresponding to the obtained number of a virtual endoscopic image or images.

13. The medical image processing apparatus, as defined in claim 8, wherein the virtual endoscopic image comprises a virtual bronchial endoscopic image, and
wherein the position of interest comprises a branching part of a bronchus or bronchi included in the three-dimensional image.

14. The medical image processing apparatus, as defined in claim 8, wherein the virtual endoscopic image comprises a virtual laparoscopic endoscopic image.

15. A medical image processing method to be performed by a medical image processing apparatus, the method comprising:
obtaining a three-dimensional image obtained by imaging an area of a patient body;
extracting from the three-dimensional image, an organ of interest within the image area of a patient body;
setting a relative degree of interest at each of a plurality of positions on a path connecting the plurality of positions in the organ of interest;
obtaining a discrimination condition for identifying, based on the set degree or degrees of interest, whether or not to generate a virtual endoscopic image corresponding to each position on the path;
identifying each position on the path which has a degree of interest greater than or equal to a threshold value based on the discrimination condition; and
generating, based on the three-dimensional image, only the virtual endoscopic image or images viewed from viewpoints corresponding to the identified positions, respectively.

16. A non-transitory computer-readable recording medium stored therein a medical image processing program for causing a computer to function as:
an image obtainment unit that is configured to obtain a three-dimensional image obtained by imaging an area of a patient body;
an extraction unit that is configured to extract, from the three-dimensional image, an organ of interest within the imaged area of the patient body;
a degree-of-interest setting unit that is configured to
set a relative degree of interest at each of a plurality of positions on a path connecting the plurality of positions in the organ of interest;
a discrimination condition obtainment unit that is configured to obtain a discrimination condition for identifying, based on the set degree or degrees of interest, whether or not to generate a virtual endoscopic image corresponding to each position on the path from the three-dimensional image; and
an image generation unit that is configured to identify each position on the path which has a degree of interest greater than or equal to a threshold value based on the discrimination condition and generate, based on the three-dimensional image, only the virtual endoscopic image or images viewed from viewpoints corresponding to the identified positions, respectively.

* * * * *